United States Patent [19]

Gebauer

[11] Patent Number: 4,625,046

[45] Date of Patent: Nov. 25, 1986

[54] ALPHA-TERTIARY NITRILES

[75] Inventor: Helmut Gebauer, Munich, Fed. Rep. of Germany

[73] Assignee: Consortium fur elektrochemische Industrie GmbH, Munich, Fed. Rep. of Germany

[21] Appl. No.: 605,889

[22] Filed: May 1, 1984

[30] Foreign Application Priority Data

Aug. 5, 1983 [DE] Fed. Rep. of Germany ....... 3328422

[51] Int. Cl.$^4$ .................... C07C 121/66; C07C 121/30
[52] U.S. Cl. ...................................... 558/388; 558/462; 252/522 R
[58] Field of Search ............ 260/465 K, 465 F, 465.9; 558/388, 462

[56] References Cited

U.S. PATENT DOCUMENTS 3,655,722 4/1972 Mitchell et al. .................. 260/465.9

OTHER PUBLICATIONS

Kieczykowski et al, Tetrahedron Letters, No. 52, pp. 4647–4650 (1975).

Primary Examiner—Dolph H. Torrence
Attorney, Agent, or Firm—Collard, Roe & Galgano

[57] ABSTRACT

Alpha-tertiary nitriles, a process for making the same, and fragrant substances containing the same, in which the nitriles having the general formula

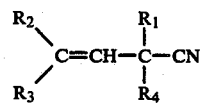

wherein
  $R_1$ represents an alkyl radical with 1–3 carbon atoms,
  $R_2$ and $R_3$ stand for hydrogen and an alkyl radical with 1–3 carbon atoms, and
  $R_4$ is an allyl or benzyl radical.

1 Claim, No Drawings

ALPHA-TERTIARY NITRILES

The present invention relates to nitriles, which, referring to the nitrile group, contain a tertiary carbon atom in alpha-position, an olefinic unit in beta-gamma-position, and an olefinic or aromatic unit in gamma'-delta'-position.

Nitriles have become well known as fragrant substances. For instance, in U.S. Pat. No. 3,655,722, the use of 3,7-dimethyl-2,6-octadienenitrile has been described as a fragrant substance. Furthermore, according to DE-OS No. 29 10 579 carbocyclic nitriles were disclosed as fragrant substances.

Another publication, "Tetrahedron Letters" No. 52, (1975, 4647–4650), mentions 2-ethenyl-2-methyl-4-pentenenitrile, without indicating a use of this substance.

It is the object of the present invention to provide fragrant substances which are easily accessible by a chemical process and which are completely synthetic.

The compounds according to the invention have the general formula

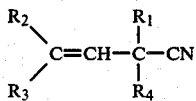

wherein $R_1$ represents an alkyl radical with 1–3 carbon atoms, $R_2$ and $R_3$ stand for hydrogen and an alkyl radical with 1–3 carbon atoms, and $R_4$ is an allylic or a benzylic radical, with the exception of 2-ethenyl-2-methyl-4-pentenenitrile.

Examples of $R_1$ are methyl-, ethyl-, n-propyl and iso-propyl radicals.

Examples of $R_2$ and $R_3$ are hydrogen and the radicals indicated for $R_1$.

Examples of $R_4$ are particularly allylic and benzylic radicals with 3–9 carbon atoms. By these, such radicals are to be understood which, referring to the nitrile group, contain in gamma'delta'-position an olefinic or aromatic unit. Examples are the allyl-, methallyl-, crotyl-, prenyl-, benzyl-, 4-methoxybenzyl-, 4-methylbenzyl-, 2,4-dimethoxybenzyl- and 2,4-dimethylbenzyl radical. A further example for $R_4$ is the diphenylmethyl radical.

Examples of compounds according to the invention are:
2-Ethenyl-2-ethyl-4-pentenenitrile
2-Ethenyl-2-n-propyl-4-pentenenitrile
2-Ethenyl-2-iso-propyl-4-pentenenitrile
2-Ethenyl-2-methyl-4-hexenenitrile
2-Ethenyl-2-ethyl-4-hexenenitrile
2-Ethenyl-2-n-propyl-4-hexenenitrile
2-Ethenyl-2-iso-propyl-4-hexenenitrile
2,5-Dimethyl-2-ethenyl-4-hexenenitrile
2-Ethyl-2-propenyl-4-hexenenitrile
2-Ethenyl-2-n-propyl-4-hexenenitrile
2-Ethenyl-2-iso-propyl-4-hexenenitrile
2,4-Dimethyl-2-ethenyl-4-pentenenitrile
2-Ethenyl-2-ethyl-4-methyl-4-pentenenitrile
2-Ethenyl-2-n-propyl-4-methyl-4-pentenenitrile
2-Ethenyl-2-iso-propyl-4-methyl-4-pentenenitrile
2-Benzyl-2-methyl-3-butenenitrile
2-Benzyl-2-ethyl-3-butenenitrile
2-Benzyl-2-ethenyl-pentanenitrile
2-Benzyl-2-ethenyl-3-methyl-butanenitrile
2-(4-Methyl-phenylmethyl)-2-methyl-3-butenenitrile
2-(2,4-Dimethylphenylmethyl)-2-methyl-3-butenenitrile
2-(4-Methoxy-phenylmethyl)-2-methyl-3-butenenitrile
2-(2,4-Dimethoxy-phenylmethyl)-2-methyl-3-butenenitrile
2-Diphenylmethyl-2-methyl-3-butenenitrile
2-Propenyl-2-methyl-4-pentenenitrile
2-Butenyl-2-methyl-4-pentenenitrile
2-Pentenyl-2-methyl-4-pentenenitrile
2-Propenyl-2-ethyl-4-pentenenitrile
2-Propenyl-2-n-propyl-4-pentenenitrile
2-Propenyl-2-iso-propyl-4-pentenenitrile
2-Butenyl-2-ethyl-4-pentenenitrile
2-Butenyl-2-propyl-4-pentenenitrile
2-Butenyl-2-iso-propyl-4-pentenenitrile
2-Pentenyl-2-ethyl-4-pentenenitrile
2-Pentenyl-2-propyl-4-pentenenitrile
2-Pentenyl-2-iso-propyl-4-pentenenitrile
2-(2'-Methyl-propenyl)-2-methyl-4-pentenenitrile
2-(2-Methylbutenyl)-2-methyl-4-pentenenitrile
2-(2-Methylpentenyl)-2-methyl-4-pentenenitrile
2-(2-Ethyl-butenyl)-2-methyl-4-pentenenitrile
2-(2-Ethyl-pentenyl)-2-methyl-4-pentenenitrile
2-(2-Propyl-pentenyl)-2-methyl-4-pentenenitrile
2-(2-Methyl-propenyl)-2-ethyl-4-pentenenitrile
2-(2-Methyl-propenyl)-2-propyl-4-pentenenitrile
2-(2-Methyl-propenyl)-2-iso-propyl-4-pentenenitrile
2-(2,3-Dimethyl-butenyl)-2-methyl-4-pentenenitrile
2-Ethyl-2-ethenyl-5-methyl-4-hexenenitrile
2-Propyl-2-ethenyl-5-methyl-4-hexenenitrile
2-Propenyl-2,5-dimethyl-4-hexenenitrile
2-Butenyl-2,5-dimethyl-4-hexenenitrile
2-Pentenyl-2,5-dimethyl-4-hexenenitrile
2-(2-Methyl-propenyl)-2,5-dimethyl-4-hexenenitrile
2-(2-Methyl-pentenyl)-2,5-dimethyl-4-hexenenitrile
2-Propenyl-2-n-propyl-5-methyl-4-hexenenitrile
2-Propenyl-2-iso-propyl-5-methyl-4-hexenenitrile
2-Propenyl-2-ethyl-5-methyl-4-hexenenitrile
2-Butenyl-2-ethyl-5-methyl-4-hexenenitrile
2-Butenyl-2-n-propyl-5-methyl-4-hexenenitrile
2-Butenyl-2-iso-propyl-5-methyl-4-hexenenitrile
2-(2-Methyl-propenyl)-2-ethyl-5-methyl-4-hexenenitrile
2-(2-Methyl-propenyl)-2-n-propyl-5-methyl-4-hexenenitrile
2-(2-Methyl-butenyl)-2-ethyl-5-methyl-4-hexenenitrile
2-(2-Methyl-butenyl)-2-iso-propyl-5-methyl-4-hexenenitrile
2-(2-Methyl-butenyl)-2,5-dimethyl-4-hexenenitrile
2-Benzyl-2-propenyl-pentanenitrile
2-Ethenyl-2-methyl-4-heptenenitrile
2-Ethenyl-2-ethyl-4-heptenenitrile
2-Ethenyl-2-n-propyl-4-heptenenitrile
2-Ethenyl-2-iso-propyl-4-heptenenitrile
2-Propenyl-2-methyl-4-heptenenitrile
2-Propenyl-2-ethyl-4-heptenenitrile
2-Propenyl-2-n-propyl-4-heptenenitrile
2-Propenyl-2-iso-propyl-4-heptenenitrile
2-(4-Methoxy-phenylmethyl)-2-ethyl-3-butenenitrile The compounds according to the invention are obtainable by alkylation of alpha-beta unsaturated nitriles under the action of phase-transfer catalysts.

A preferred method of producing the compounds of the general formula

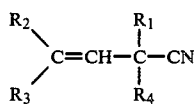

wherein
R₁ represents an alkyl radical with 1-3 carbon atoms,
R₂ and R₃ stand for hydrogen and an alkyl radical with 1-3 carbon atoms, and
R₄ is an allylic or benzylic radical,
is characterized by reacting compounds of the general formula

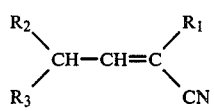

wherein R₁, R₂ and R₃ have the same meaning as indicated above, with compounds of the formula

R₄X wherein R₄ has the meaning indicated above, and X stands for chloride, bromide or iodide, in an organic-alkaline 2-phase system in the presence of a phase-transfer catalyst.

Examples of the compounds of the general formula

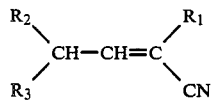

are especially 2-methyl-2-butenenitrile, 2-ethyl-2-butenenitrile, 2-ethylidenepentanenitrile, 2-methyl-2-pentenenitrile, 2-ethyl-2-pentenenitrile, 2-propyl-2-pentenenitrile, 2,4-dimethyl-2-pentenenitrile, 2-methyl-2-hexenenitrile, and 2-methyl-2-heptenenitrile among others.

The nitriles serving as starting materials are obtainable by cyanhydride formation with ketones and subsequent splitting off of water. The production of appropriate ketones

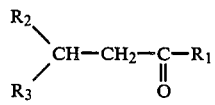

is well known and conventional according to the state of the art.

They are partly commercially available substances. The ketones may, e.g., be made as aldol-condensation products or advantageously from appropriate carboxylic acid mixtures, which are passed over alumina- or thorium oxide catalysts at elevated temperatures, forming by condensation and de-carboxylation the corresponding ketones.

Examples of compounds of the formula R₄X, which in the following are called alkylating agents, are allyl chloride, allyl bromide, methallyl chloride, crotyl chloride, prenyl chloride, benzyl chloride, 4-methylbenzyl chloride, 4-methoxybenzyl chloride, 2,4-dimethylbenzyl chloride, 2,4-dimethoxybenzyl chloride, diphenylmethyl bromide among others.

The organic/alkaline 2-phase system is formed by an inert organic solvent, immiscible with water, and a 5-50%, especially 20-50%, aqueous solution or an alkali metal hydroxide present in solid state. Examples of inert solvents are benzene, toluene, xylene, cyclohexane, petrol ether, benzine and the like.

Examples of alkali metal hydroxides are particularly NaOH, KOH and the like.

In the process of the invention all the phase-transfer catalysts may be used which have conventionally been used to such reactions. Examples are crown ether, quaternary ammonium and phosphonium salts, especially tetrabutylammonium bromide. The phase-transfer catalysts are used in amounts of 0.5-5% Molar, especially 2-3% Molar in every case referring to the alkylating agent.

The amounts of alpha-beta-unsaturated nitriles to be alkylated and the alkylating agent are about equimolar. Frequently, however, an excess quantity of alkylating agent is used, for instance, 1.1-1.5 moles of alkylating agent per mole of nitrile used.

When calculated with reference to the alkylating agent, about equimolar amounts of alkali metal hydroxide are necessary. It is however advantageous to use 1.1-1.5 moles of alkali metal hydroxide per mole of alkylating agent used.

In principle, the order of adding the reaction components to the reaction mixture may be arbitrary. In a preferred mode of carrying out the process, the organic-alkaline 2-phase system, together with the phase-transfer catalyst, is first introduced and a mixture of the other reaction components is added in doses.

Alternatively, it is just as well to introduce all the organic reaction components first and then to add in doses the alkali metalhydroxide, especially in solid state.

The reaction temperatures are, in general, maintained between 0° and 150° C., particularly between 20° and 110° C. Frequently an optimal ratio of reaction time and yield is achieved at 60°-90° C.

The processing of the reaction mixture is brought about by a conventional technique. Usually, the phases are separated and the organic phase is subjected to fractional distillation. The invention furthermore relates to the use of the compounds as fragrant substances. For that purpose, 2-ethenyl-2-methyl-4-pentenenitrile is not excluded, although its odor has been found not to be satisfactory and not useful as a practical matter.

With the compounds according to the invention, perfumes may be obtained, having new, mostly fruity-lemony, but also fresh flower-like aromas. In addition, some of the products have a metallic character which is sometimes desirable in compositions.

In the following, the invention is described more fully in a number of examples, but it should be understood that these are given by way of illustration and not of limitation.

EXAMPLE 1

2,5-Dimethyl-2-ethenyl-4-hexenenitrile

Into a 1 liter 4-neck flask equipped with a stirrer, reflux cooler, and dropping funnel, 48 g (1.2 moles) of solid sodium hydroxide, 200 ml of toluene and 10 g of tetrabutyl ammonium bromide were first introduced, and heated to 70° C. Within 2 hours, a mixture of 81 g (1 mole) of 2-methyl-2-butenenitrile, and 125.4 g (1.2 moles) of prenyl chloride were added dropwise while stirring. Thereupon, the reaction mixture was further stirred for 3 hours at 75° C. For processing the reaction mixture, excess sodium hydroxide and sodium chloride formed in the reaction were first washed out with water. Then the phases were separated, and the organic phase washed with water to neutrality. After withdrawing the solvent, distillation took place in vacuo in a 30 cm. Vigreux column. The yield in desired product amounted to 62 g, ; corresponding to 41% of the theoretical.

Colorless oil, Bp. at 12 torr, 77° C.

Aroma: strong, lemony, fruity-sweet, slightly metallic.

EXAMPLE 2

2-Methyl-2-phenylmethyl-3-butenenitrile

Into a 500 ml 4-neck flask, equipped with a stirrer, reflux cooler, dropping funnel and water separator, 126.5 g (1 mole) of benzylchloride, 81 g (1 mole) of 2-methyl-2-butene-nitrile, 100 ml of toluene, and 10 g of tetrabutylammonium bromide were first introduced and heated to reflux. To this mixture, 40 g (1 mole) of solid sodium hyroxide were added in portions. The reaction mixture was then maintained one more hour at reflux. Thereupon, it was washed to neutrality with water, the phases were separated and the organic phase distilled as described in Example 1. The yield in desired product was 103.5 g, corresponding to 61% of the theoretical.

Colorless oil, Bp 76°-77° C. at 0.05 torr.

Aroma: Long-lasting, lemony-fruity fragrance, with flower-like side aroma.

EXAMPLE 3

2-(2-Propenyl)-2-propyl-3-pentenenitrile

Into a 250 ml 4-neck flask equipped with stirrer, reflux cooler and dropping funnel, 20 g (0.5 moles) of solid sodium hydroxide, 80 ml of toluene and 5 g of tetrabutylammonium bromide are first introduced and heated to 80° C. To this 2-phase system, a mixture of 50 g (0.41 moles) of 2-propyl-2-pentenenitrile and 31.4 g (0.41 moles) of allyl chloride were added in doses within 30 minutes. The reaction mixture was maintained for 2 more hours at a temperature of 75° C. Further work proceeded as in Example 1. A yield of 24 g of desired product, corresponding to 29.4% of the theoretical, was obtained.

Colorless oil, boiling range at 12 to 87°-90° C.

Aroma: strong fruity-lemony like green stalks.

EXAMPLE 4

5-Methyl-2-(1-propenyl)-2-propyl-4-hexenenitrile

In analogy to Example 1, 64 g (1.6 moles) of NaOH, 200 ml of toluene, and 15 g of tetrabutylammonium bromide were first introduced and heated to 75° C. To this mixture was added a mixture of 147.6 g (1.2 moles) of 2-propyl-2-pentenenitrile and 157 g (1.5 moles) of prenyl chloride within 2 hours in individual doses. The reaction mixture was further heated for 3 hours at 85° C. and subsequently processed according to Example 1. The yield in desired product was 103 g, corresponding to 44.9% of the theoretical.

Colorless oil, boiling range at 0.05 torr, 60°-65° C.

Aroma: lemony, fruity-sweet, slightly fatty.

While only several embodiments and examples of the present invention have been described, it is obvious that many changes and modifications may be made thereunto, without departing from the spirit and scope of the invention.

What is claimed is:

1. A compound which is selected from
2,5-dimethyl-2-ethenyl-4-hexenenitrile,
2-methyl-2-phenylmethyl-3-butenenitrile,
2-(2-propenyl)-2-propyl-3-pentenenitrile, and
5-methyl-2-(1-propenyl)-2-propyl-4-hexenenitrile.

* * * * *